United States Patent [19]
Hoard et al.

[11] Patent Number: 5,514,826
[45] Date of Patent: May 7, 1996

[54] VINYL SULFENIC ACID DERIVATIVES

[75] Inventors: David W. Hoard, Lafayette; Wayne D. Luke, West Lafayette, both of Ind.

[73] Assignee: Eli Lilly and Company, Indianapolis, Ind.

[21] Appl. No.: 483,607

[22] Filed: Jun. 7, 1995

[51] Int. Cl.$^6$ .................................. C07F 7/08; C07F 7/18
[52] U.S. Cl. ........................... 556/428; 558/62; 564/102; 568/23; 568/25; 540/604; 544/158; 546/192; 546/236; 548/542
[58] Field of Search ............................. 556/428; 558/62; 564/102; 568/23, 25; 540/604; 544/158; 546/192, 236; 548/542

[56] References Cited

U.S. PATENT DOCUMENTS

| | | | |
|---|---|---|---|
| 4,380,635 | 4/1983 | Peters | 546/202 |
| 4,835,297 | 5/1989 | Deschler et al. | 556/428 X |

OTHER PUBLICATIONS

Campaigne and Cline, "A New Synthesis of Thiophenes and Condensed Thiophenes by Ring Closure of Disulfides", *J. Org. Chem.*, 21, 39–44 (1956).

Campaigne, "Thiophenes and their Benzo Derivatives: (iii) Synthesis and Applications", in Comprehensive Heterocyclic Chemistry, vol. 4, Part 3, 863–894 (1984).

Ando, "Prolysis of Styryl Sulphoxides and Sulphoxides and Sulphides. Formation of Benzothiophen Derivatives via Intramolecular Cyclization of Thiyl Radicals", *J. Chem. Soc., Chem. Comm.*, 704–5 (1975).

Shelton and Davis, "t–Butylsulfenic Acid", *J. Am. Chem. Soc.*, 89(3), 718–19 (1967).

Mazzanti et al., "Intramolecular Trapping Reactions of Vinylsulfenic Acid Tautomers of Enethiolisable Sulfines", *J. Chem. Soc., Perkin. Trans. I*, 3299–3304 (1994).

Mukaiyama and Saigo, "A Convenient Method for the Preparation of Vinyl Sulfides from Carbonyl Compounds by Using TiCl$_4$", *Chem Letters*, 479–482 (1973).

Kodama et al., "Attractive Interaction between Aliphatic and Aromatic Systems", *Tetrahedron Letters*, 2105–08 (1977).

Casey and Manage, "Stereoselective Conjugate Additions of Benzyl Sulphoxides to α,β–Unsaturated Esters", *Tetrahedron Letters*, 30(49), 6919–22 (1989).

Casey et al., "Stereoselective Conjugate Additions of Sulphoxide Stabilised Carbanions to α, β–Unsaturated Esters", *Tetrahedron Letters*, 29(45), 5821–24 (1988).

Davis et al., "Chemistry of Sulfenic Acids. 1. Synthesis of Trimethylsilyl Arenesulfenates (Arenesulfenic Acids)", *J. Org. Chem.*, 45, 1650–53 (1980).

Davis and Friedman, "Trimethylsilyl 2–Nitrobenzenesulfenate (2–Nitrobenzensulfenic Acid)", *J. Org. Chem.*, 41(5), 897–898 (1976).

Barton and Zika, "Adducts of Acetylenes and Sulfur Dichloride", *J. Org. Chem.*, 35, 1729–33 (1970).

Guindon et al., "Direct Synthesis of Thioethers from Thiols and Alcohols", *J. Org. Chem.*, 48, 1357–59 (1983).

Pyne and Boche, "Stereoselective Reactions of Lithium and Zinc tert–Butyl Phenylmethyl Sulfoxide with Carbonyl Compounds and Imines", *J. Org. Chem.*, 54, 2663–67 (1989).

*Primary Examiner*—Paul F. Shaver
*Attorney, Agent, or Firm*—James P. Leeds; David E. Boone

[57] ABSTRACT

The present invention is directed to novel vinyl sulfenic acid derivatives, useful for the synthesis of benzo[b]thiophenes, in particular 2-arylbenzo[b]thiophenes.

17 Claims, No Drawings

VINYL SULFENIC ACID DERIVATIVES

BACKGROUND OF THE INVENTION

The present invention is directed to novel vinyl sulfenic acid derivatives, useful for the synthesis of benzo[b]thiophenes, in particular 2-arylbenzo[b]thiophenes.

Benzo[b]thiophenes have been prepared by a number of different synthetic routes. One of the most widely used methods is the oxidative cyclization of o-mercaptocinnamic acids. This route is limited to the preparation of benzo[b]thiophene-2-carboxylates. 2-Phenylbenzo[b]thiophenes are prepared by acid-catalyzed cyclization of 2-phenylthioacetaldehyde dialkyl acetals. Unsubstituted benzo[b]thiophenes are prepared by catalytic condensation of styrene and sulfur. 3-Substituted benzo[b]thiophenes are prepared by acid-catalyzed cyclization of arylthiomethyl ketones; however, this route is limited to the preparation of 3-alkylbenzo[b]thiophenes. See Campaigne, "Thiophenes and their Benzo Derivatives: (iii) Synthesis and Applications," in Comprehensive Heterocyclic Chemistry (Katritzky and Rees, eds.), Volume IV, Part III, 863–934 (1984). 3-Chloro-2-phenylbenzo[b]thiophene is prepared by the reaction of diphenylacetylene with sulfur dichloride. Barton and Zika, *J. Org. Chem.*, 35, 1729–1733 (1970). Benzo[b]thiophenes have also been prepared by pyrolysis of styryl sulfoxides. However, low yields and extremely high temperatures make this route unsuitable for production-scale syntheses. See Ando, *J. Chem. Soc., Chem. Comm.*, 704–705 (1975).

Sulfenic acids have been postulated as key intermediates in a variety of chemical reactions; however, very few examples exist of the isolation of these compounds. See Shelton and Davis, *J. Am. Chem. Soc.*, 89(3), 718–719 (1968) and Davis et al., *J. Am. Chem. Soc.*, 100, 2844 (1978). Sulfenic acids have been generated in situ, and intramolecularly or intermolecularly cyclyzed with olefins and acetylenes. See Mazzanti et al., *J. Chem. Soc., Perkin Trans. I*, 3299–3004 (1944) and Davis et al., *J. Org. Chem.*, 45, 1650–1653 (1980). A series of trimethylsilyl arenesulfenates have been prepared from the corresponding N-benzylidenearenesulfinamides; however, the yield of the trimethylsilyl ester was generally very low. Davis et al., *J. Org. Chem.*, 45, 1650–1653 (1980).

The preparation of 6-hydroxy-2-(4-hydroxyphenyl)benzo[b]thiophenes was described in U.S. Pat. Nos. 4,133,814 and 4,380,635. One process described in these patents is the acid-catalyzed intramolecular cyclization/rearrangement of α-(3-methoxyphenylthio)-4-methoxyacetophenone. The reaction of this starting compound in neat polyphosphoric acid at about 85° C. to about 90° C. gives an approximate 3:1 mixture of two regioisomeric products: 6-methoxy-2-(4-methoxyphenyl)benzo[b]thiophene and 4-methoxy-2-(4-methoxyphenyl)benzo[b]thiophene. These isomeric benzo[b]thiophenes co-precipitate from the reaction mixture, producing a mixture containing both compounds. To obtain a single regioisomer, the regioisomers must be separated, such as by chromatography or fractional crystallization. Therefore, there currently exists a need for an efficient and regiospecific synthesis of 2-arylbenzo[b]thiophenes from readily available starting materials.

SUMMARY OF THE INVENTION

The present invention is directed to novel vinyl sulfenic acid derivatives: novel sulfenate silyl esters, sulfenamides, and disulfides. Specifically, the present invention is directed to a compound of the formula

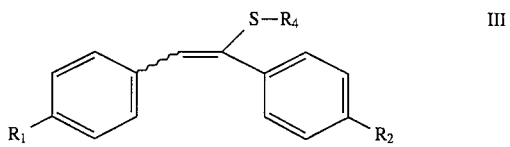

wherein:

$R_1$ is hydrogen, $C_1$–$C_4$ alkoxy, arylalkoxy, halo, or amino;

$R_2$ is hydrogen, $C_1$–$C_4$ alkoxy, arylalkoxy, halo, or amino;

$R_4$ is $OSi(R)_3$, $NR_5R_6$, or $SR_8$;

each R is independently $C_1$–$C_6$ alkyl aryl, or arylalkyl;

$R_5$ and $R_6$ are independently hydrogen, $C_1$–$C_6$ alkyl, arylalkyl, or aryl, or $R_5$ and $R_6$ together with the nitrogen atom form a ring selected from piperidine, pyrrolidine, morpholine, or hexamethylimine; and $R_8$ is $C_1$–$C_6$ alkyl, aryl, or arylalkyl. Thus, the present invention includes individually the E and Z isomers, or mixtures thereof, of the formula III compounds. These E and Z regioisomers are represented by the following structures:

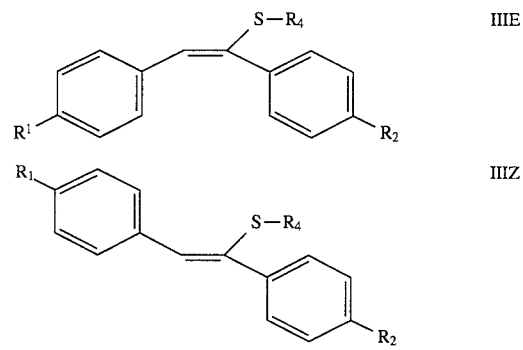

Another aspect of the present invention is a process for the synthesis of a compound of the formula

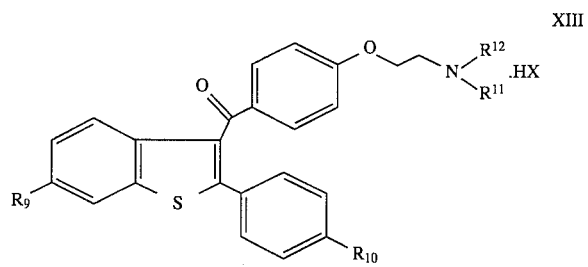

wherein:

$R_9$ is hydrogen, halo, amino, or hydroxyl;

$R_{10}$ is hydrogen, halo, amino, or hydroxyl;

$R_{11}$ and $R_{12}$ are independently $C_1$–$C_4$ alkyl, or $R_{11}$ and $R_{12}$ together with the adjacent nitrogen atom form a heterocyclic ring selected from the group consisting of pyrrolidino, piperidino, hexamethyleneimino, and morpholino; and HX is HCl or HBr;

comprising the steps of:

(a) cyclizing in the presence of an acid catalyst a compound of the formula

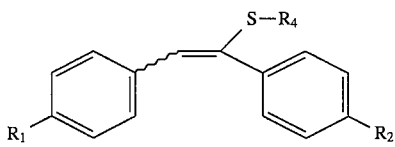

wherein:
$R_1$ is hydrogen, $C_1$–$C_4$ alkoxy, arylalkoxy, halo, or amino;
$R_2$ is hydrogen, $C_1$–$C_4$ alkoxy, arylalkoxy, halo, or amino; and
$R_4$ is $OSi(R)_3$, $NR_5R_6$, or $SR_8$;
each R is independently $C_1$–$C_6$ alkyl, aryl, or arylalkyl;
$R_5$ and $R_6$ are independently hydrogen, $C_1$–$C_6$ alkyl, or aryl, or $R_5$ and $R_6$ together with the nitrogen atom form a ring selected from piperidine, pyrrolidine, morpholine, and hexamethylimine; and
$R_8$ is $C_1$–$C_6$ alkyl, aryl, or arylalkyl; to prepare a benzothiophene compound of the formula

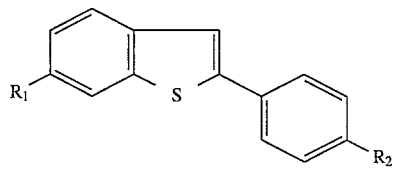

wherein $R_1$ and $R_2$ are as defined above;

(b) acylating said benzothiophene compound with an acylating agent of the formula

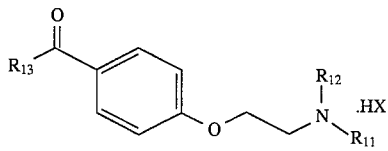

wherein:
$R_{11}$, $R_{12}$, and HX are as defined previously; and
$R_{13}$ is chloro, bromo, or hydroxyl; in the presence of $BX'_3$, wherein X' is chloro or bromo;

(c) when $R_1$ and/or $R_2$ is $C_1$–$C_4$ alkoxy or arylalkoxy, dealkylating one or more phenolic groups of the acylation product of step (b) by reacting with additional $BX'_3$, wherein X' is as defined above; and (d) isolating the formula XIII compound.

DETAILED DESCRIPTION OF THE INVENTION

The term "acid catalyst" represents a Lewis acid or a Brønsted acid. Representative Lewis acids are zinc chloride, zinc iodide, aluminum chloride, and aluminum bromide. Representative Brønsted acids include: inorganic acids, such as sulfuric and phosphoric acids; carboxylic acids, such as acetic and trifluorocetic acids; sulfonic acids, such as methanesulfonic, benzenesulfonic, 1-naphthalenesulfonic, 1-butanesulfonic, ethanesulfonic, 4-ethylbenzenesulfonic, 1-hexanesulfonic, 1,5-naphthalenedisulfonic, 1-octanesulfonic, camphorsulfonic, trifluoromethanesulfonic, and p-toluenesulfonic acids; and polymeric arylsulfonic acids, such as Nafion®, Amberlyst®, or Amberlite®. The preferred acids for use in catalyzing the processes of the present invention are sulfonic or polymeric sulfonic acids. More preferably, the acid catalysts are sulfonic acids, such as methanesulfonic acid, benezenesulfonic acid, camphorsulfonic acid, and p-toluenesulfonic acid. The most preferred acid catalyst is p-toluenesulfonic acid.

In the above formula, the term "$C_1$–$C_4$ alkoxy" represents groups such as methoxy, ethoxy, n-propoxy, isopropoxy, n-butoxy, t-butoxy, and like groups. The term "halo" refers to fluoro, chloro, bromo, or iodo groups.

The term "$C_1$–$C_6$ alkyl" represents a straight or branched alkyl chain having from one to six carbon atoms. Typical $C_1$–$C_6$ alkyl groups include methyl, ethyl, n-propyl, isopropyl, n-butyl, isobutyl, sec-butyl, t-butyl, n-pentyl, isopentyl, n-hexyl, 2-methylpentyl, and the like. The term "$C_1$–$C_4$ alkyl" represents a straight or branched alkyl chain having from one to four carbon atoms, and includes methyl, ethyl, n-propyl, isopropyl, n-butyl, sec-butyl, i-butyl, and t-butyl.

The term "aryl" represents groups such as phenyl and substituted phenyl. The term "substituted phenyl" represents a phenyl group substituted with one or more moieties chosen from the group consisting of halo, hydroxy, nitro, $C_1$–$C_4$ alkyl, $C_1$–$C_4$ alkoxy, trichloromethyl, and trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 2,4-dinitrophenyl, 4-methylphenyl, 4-ethylphenyl, 4-methoxyphenyl, 4-propylphenyl, 4-n-butylphenyl, 4-t-butylphenyl, 3-fluoro-2-methylphenyl, 2,3-difluorophenyl, 2,6-difluorophenyl, 2,6-dimethylphenyl, 2 -fluoro-5-methylphenyl, 2,4,6-trifluorophenyl, 2-trifluoromethylphenyl, 2-chloro-5-trifluoromethylphenyl, 3,5-bis(trifluoromethyl)phenyl, 2-methoxyphenyl, 3-methoxyphenyl, 3,5-dimethoxyphenyl, 4-hydroxy-3-methylphenyl, 3,5-dimethyl, 4-hydroxyphenyl, 2-methyl-4-nitrophenyl, 4-methoxy-2-nitrophenyl, and the like.

The term "arylalkyl" represents a $C_1$–$C_4$ alkyl group bearing one or more aryl groups. Representatives of this group include benzyl, o-nitrobenzyl, p-nitrobenzyl, p-halobenzyl (such as p-chlorobenzyl, p-bromobenzyl, p-iodobenzyl), 1-phenylethyl, 2 -phenylethyl, 3 -phenylpropyl, 4-phenylbutyl, 2 -methyl -2 -phenylpropyl, (2,6 -dichlorophenyl)methyl, bis(2,6-dichlorophenyl) methyl, (4-hydroxyphenyl)methyl, (2,4-dinitrophenyl)methyl, diphenylmethyl, triphenylmethyl, (p-methoxyphenyl)-diphenylmethyl, bis(p-methoxyphenyl)methyl, bis(2 -nitrophenyl) methyl, and the like.

The term "arylalkoxy" represents a $C_1$–$C_4$ alkoxy group bearing one or more aryl groups. Representatives of this group include benzyloxy, o-nitrobenzyloxy, p-nitrobenzyloxy, p-halobenzyloxy (such as p-chlorobenzyloxy, p-bromobenzyloxy, p-iodobenzyloxy ), 1-phenylethoxy, 2-phenylethoxy, 3-phenylpropoxy, 4-phenylbutoxy, 2-methyl-2-phenylpropoxy, (2,6-dichlorophenyl)methoxy, bis (2,6-dichlorophenyl)methoxy, (4-hydroxyphenyl)methoxy, (2,4-dinitrophenyl)methoxy, diphenylmethoxy, triphenylmethoxy, (p-methoxyphenyl)diphenylmethoxy, bis(p-methoxyphenyl)methoxy, bis(2-nitrophenyl)methoxy, and the like.

The term "thermally-labile or acid-labile $C_2$–$C_{10}$ alkyl, $C_4$–$C_{10}$ alkenyl, or aryl($C_1$–$C_{10}$ alkyl) group" represents a group that is readily removed from the sulfoxide (SO) group under heating or by treatment with the acid catalyst. The thermally-labile or acid-labile $C_2$–$C_{10}$ alkyl groups are straight or branched alkyl chains having from two to ten carbon atoms and having at least one beta-hydrogen atom.

Representative thermally-labile or acid-labile $C_2$–$C_{10}$ alkyl groups include ethyl, n-propyl, i-propyl, 1,1-dimethylpropoyl, n-butyl, sec-butyl, t-butyl, 1,1-dimethylbutyl, 2-methylbutyl, 3-methylbutyl, 1-methylbutyl, 1,2-dimethylbutyl, 1,3-dimethylbutyl, 2,4-dimethylbutyl, 3,3-dimethylbutyl, n-pentyl, 1-methylpentyl, 2-methylpentyl, 3-methylpentyl, 4-methylpentyl, n-hexyl, and the like. The thermally-labile or acid-labile $C_4$–$C_{10}$ alkenyl groups are straight or branched alkenyl chains having from four to ten carbon atoms, at least one site of unsaturation, and either a beta-hydrogen or delta-hydrogen atom. Representative thermally-labile or acid-labile $C_4$–$C_{10}$ alkenyl groups include 2-butenyl, 3-butenyl, 2-methyl-2-butenyl, 3-methyl-2-butenyl, 2-methyl-3-butenyl, 2-pentenyl, 3-pentenyl, 4-pentenyl, 2-methyl-2-pentenyl, 3-methyl-2-pentenyl, 4-methyl-2-pentenyl, 2-methyl-3 -pentenyl, 3-methyl-3-pentenyl, 4-methyl-3-pentenyl, 2 -methyl-4-pentenyl, 3-methyl-4-pentenyl, 4-methyl-4-pentenyl, 2-hexenyl, 3-hexenyl, 4-hexenyl, 5-hexenyl, and the like. The term thermally-labile or acid-labile aryl($C_1$–$C_{10}$ alkyl) represents thermally-labile or acid-labile $C_2$–$C_{10}$ alkyl groups additionally containing one or more aryl groups and aryl-substituted methyl groups. Representative aryl($C_1$–$C_{10}$ alkyl) groups include benzyl, diphenylmethyl, triphenylmethyl, p-methoxybenzyl, 2-phenylethyl, 2-phenyl-propyl, 3-phenylpropyl, and the like.

One group of compounds of the present invention are sulfenate silyl esters. In particular, the formula III compounds, where $R_4$ is OSi $(R)_3$ and each R is independently $C_1$–$C_6$ alkyl, aryl, or arylalkyl, and the formula IV compounds are silyl esters of sulfenic acids. The preferred sulfenate silyl esters are abbreviated using nomenclature well recognized in the chemical arts, as shown in the following table.

TABLE 1

| abbreviation | silyl group |
| --- | --- |
| TMS | trimethylsilyl |
| TES | triethylsilyl |
| TIPS | triisopropylsilyl |
| DMIPS | dimethylisopropylsilyl |
| DEIPS | diethylisopropylsilyl |
| TDS | dimethylhexylsilyl |
| TBDMS | t-butyldimethylsilyl |
| TBDPS | t-butyldiphenylsilyl |
| TBS | tribenzylsilyl |
| TPS | triphenylsilyl |
| DPMS | diphenylmethylsilyl |
| TBMPS | t-butyldi(methoxyphenyl)silyl |

The term "silylating reagent" represents a compound, or a combination of compounds, used to convert the intermediate sulfenic acid to a sulfenate silyl ester. Representative silylating reagents include bis(trialkylsilyl)ureas, such as 1,3-bis(trimethylsilyl)urea, 1,3-bis(triethylsilyl)urea, 1,3-bis(dimethylisopropylsilyl)urea, 1,3-bis(triisopropylsilyl)urea; 1,3-bis (diethylisopropylsilyl) urea; 1,3-bis)rdimethylhexylsilyl)urea, and 1,3-bis(t-butyldimethylsilyl)urea; bis(triarylsilyl)ureas, such as 1,3 -bis(triphenylsilyl)urea; bis(diarylalkylsilyl)ureas, such 1,3-bis(diphenylmethylsilyl)urea and 1,3-bis (t-butyldiphenylsilyl) urea; and hexaalkyldisilylzanes, such as hexamethyldisilylzane; or combination of a hexaalkyldisilylzane and a catalytic amount of a chlorotrialkylsilane, such as chlorotrimethylsilane.

The starting compounds for the compounds of the present invention can be prepared by a number of routes. One method for preparing the formula II compounds is shown in Scheme 1.

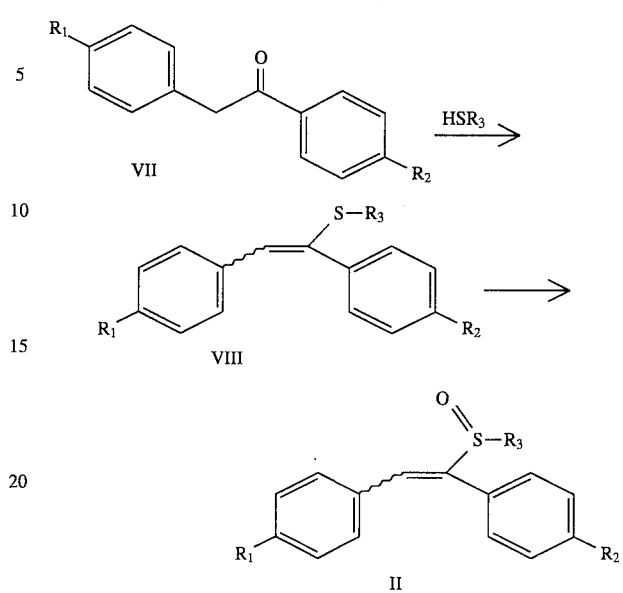

Scheme 1

Generally, a formula VII compound is converted to a styryl sulfide by reaction with a mercaptan of the formula $HSR_3$ in the presence of a Lewis acid. The formula VIII compound is then oxidized to a styryl sulfoxide, a compound of formula II compound.

More specifically, a formula VII compound, wherein $R_1$ and $R_2$ are as defined above, is treated with a Lewis acid, such as titanium(IV) chloride. This reaction is carried out in an anhydrous organic solvent, such as dry tetrahydrofuran, at a temperature of about 0° C. to about 35° C. After about 15 minutes to about one hour, the reaction mixture is treated with an amine base and a mercaptan of the formula $HSR_3$, where $R_3$ is a thermally-labile or acid-labile $C_1$–$C_{10}$ alkyl, $C_4$–$C_{10}$ alkenyl, or aryl($C_1$–$C_{10}$ alkyl) group. Preferably, the mercaptan and amine base are added as a solution in the reaction solvent. A representative amine base is triethylamine. After the addition of the mercaptan and amine base, the reaction is generally heated to a temperature of about 35° C. to about 65° C., preferably at about 50° C. The products of this reaction can be purified using techniques well known in the chemical arts, such as by crystallization or chromatography.

The formula VIII compound, where $R_1$, $R_2$, and $R_3$ are as defined above, is then oxidized to produce the formula II compounds. Suitable oxidizing agents for this reaction are peracids, such as peracetic acid and m-chloroperoxybenzoic acid, and hydrogen peroxide. This oxidation reaction is typically run in an organic solvent, such as toluene, methylene chloride, chloroform, or carbontetrachloride. When a peracid is used as the oxidant, the reaction is generally carried out at a temperature of about −30° C. to about 15° C., preferably at about −20° C. The products of the reaction are easily purified by recrystallization. When $R_3$ is t-butyl, the crystalline product of this reaction sequence is the E regioisomer of formula II.

When $R_3$ has a tertiary carbon adjacent to the sulfur atom, the Z regioisomer of the formula II compounds can be prepared selectively by a second route as shown in Scheme

II.

Scheme 2

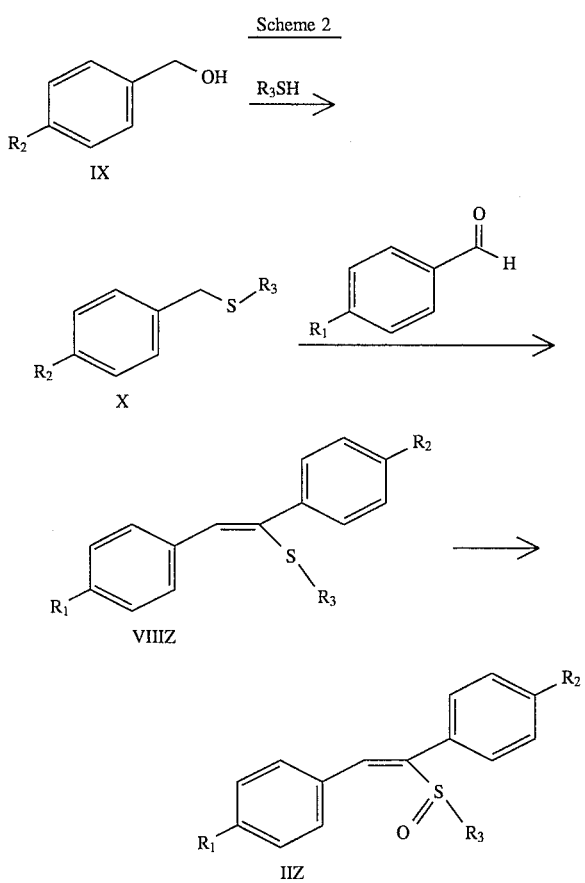

Generally, a benzyl alcohol, a formula IX compound, is reacted with a mercaptan of the formula $R_3SH$ to produce a benzyl sulfide, a formula X compound. This benzyl sulfide is reached with a strong base, forming a benzylic anion, which is condensed with a benzaldehyde. This condensation product is reacted with an acid chloride and the resulting intermediate treated with a second strong base to produce a styryl sulfide, a formula VIIIZ compound. This styryl sulfide is then oxidized with an oxidizing agent to produce the formula IIZ compound.

The first step in the synthesis of the Z styryl sulfoxide compounds is the conversion of a benzyl alcohol to a benzyl sulfide, formula X compound. The reaction of the formula IX compound, where $R_2$ is as defined above, with a mercaptan of the formula $R_3SH$, wherein $R_3$ is a thermally-labile or acid-labile $C_2$–$C_{10}$ alkyl, $C_4$–$C_{10}$ alkenyl, or aryl($C_1$–$Cl_{10}$ alkyl) group having a tertiary carbon atom adjacent to the sulfur atom, in the presence of a Lewis acid produces the benzyl sulfide, a formula X compound. Suitable Lewis acids for this transformation are zinc bromide, zinc chloride, zinc iodide, ferric chloride, titanium(IV) chloride, aluminum trichloride, and aluminum tribromide, preferably zinc iodide. The reaction is generality carried out in an organic solvent, such as 1,2-dichloroethane or methylene chloride. When the reaction is carried out at room temperature, the reaction is complete after about 18 hours.

The benzyl sulfide is reacted with a strong base to form a benzylic anion. Suitable strong bases for this reaction include metal alkoxides, such as sodium methoxide, sodium ethoxide, lithium ethoxide, lithium t-butoxide, and potassium t-butoxide; sodium hydride; and alkyllithiums, such as n-butyllithium, t-butyllithium, sec-butyllithium, and methyllithium. The preferred strong base for this reaction is n-butyllithium. The preferred solvent for this reaction is dry tetrahydrofuran. When n-butyllithium is used as the strong base, the reaction is carried out at a temperature of about −35° C. to about −15° C.

The benzylic anion is condensed with a benzaldehyde to prepare an intermediate condensation product. The benzaldehyde has the general formula p-$R_1$($C_6H_4$)CHO, wherein $R_1$ is hydrogen, $C_1$–$C_4$ alkoxy, arylalkoxy, halo, or amino. Preferably, the benzylic anion is prepared and the condensation product is formed in situ by adding the benzaldehyde to the cold solution of the benzylic anion.

The condensation product is treated with an acid chloride to produce an intermediate compound. Representative acid chlorides include acyl chlorides, such as acetyl chloride and benzoyl chloride; sulfonyl chlorides, such as methanesulfonyl chloride, benzenesulfonyl chloride, 1-butanesulfonyl chloride, ethanesulfonyl chloride, isopropylsulfonyl chloride, and p-toluenesulfonyl chloride; alkoxycarbonyl chlorides, such as methoxycarbonyl chloride and benzyloxycarbonyl chloride; and dialkylaminocarbonyl chlorides, such as N,N-dimethylaminocarbonyl chloride; preferably a sulfonyl chloride. Preferably, methanesulfonyl chloride is added to the reaction mixture shortly after formation of the condensation product.

This intermediate compound is reacted with a second strong base to produce a styryl sulfide, a formula VIIIZ compound where $R_1$, $R_2$, and $R_3$ are as defined above. Suitable strong bases for this reaction include metal alkoxides, such as sodium methoxide, sodium ethoxide, lithium ethoxide, lithium t-butoxide, and potassium t-butoxide; sodium hydride; alkyllithiums, such as n-butyllithium, t-butyllithium, sec-butyllithium, and methyllithium; and metal amides, such as sodium amide, magnesium diisopropylamide, and lithium diisopropylamide. The preferred strong base for this reaction is potassium t-butoxide. Generally, this reaction is carried out at about 15° C. to about room temperature, preferably at room temperature.

The styryl sulfide is oxidized to prepare the corresponding styryl sulfoxide. Suitable oxidizing agents for this reaction are peracids, such as peracetic acid and m-chloroperoxybenzoic acid; organic peroxides, such as t-butyl peroxide; and hydrogen peroxide. Preferably the oxidizing agent is peracetic acid. This oxidation is typically carried out in an organic solvent, such as toluene, benzene, xylene, methanol, ethanol, methylacetate, ethylacetate, methylene chloride, 1,2-dichloroethane, or chloroform; preferably methylene chloride. This oxidation can be carried out at a temperature of about −40° C. to about 0° C.

Alternatively, when $R_3$ has a tertiary carbon adjacent to the sulfur atom, the benzyl sulfide intermediate (formula X compound) can be used to produce a mixture of E and Z isomers of the styryl sulfoxides, the formula II compounds. This synthesis is outlined is Scheme 3.

Scheme 3

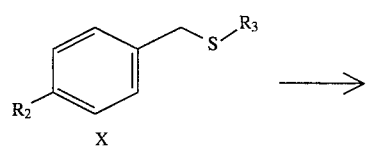

-continued
Scheme 3

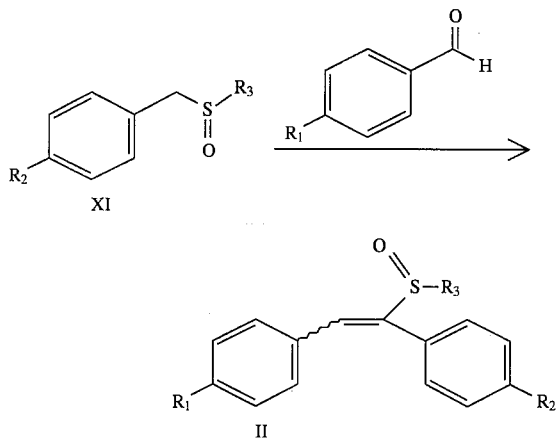

The benzyl sulfide, prepared as described above, is oxidized to produce the corresponding benzyl sulfoxide. This benzyl sulfoxide is reacted with a strong base, and the resulting anion condensed with a benzaldehyde. The condensation product is reacted with an acid chloride and the resulting intermediate compound reacted with a second strong base to produce the styryl sulfoxide.

The benzyl sulfide, the formula X compound, wherein $R_2$ is as defined above and $R_3$ is a thermally-labile or acid-labile $C_2$–$C_{10}$ alkyl, $C_4$–$C_{10}$ alkenyl, or aryl($C_1$–$C_{10}$ alkyl) group having a tertiary carbon atom adjacent to the sulfur atom, is oxidized to produce the corresponding benzyl sulfoxide, formula XI compound. Suitable oxidizing agents for this reaction are peracids, such as peracetic acid and m-chloroperoxybenzoic acid; organic peroxides, such as t-butyl peroxide; and hydrogen peroxide. Preferably the oxidizing agent is peracetic acid. This oxidation is typically carried out in an organic solvent, such as toluene, benzene, xylene, methanol, ethanol, methylacetate, ethylacetate, methylene chloride, 1,2-dichloroethane, or chloroform; preferably at a temperature of about $-30°$ C. to about $5°$ C.

The benzyl sulfoxide, formula XI compound wherein $R_2$ and $R_3$ are as defined above, is reacted with a strong base to produce a benzylic anion. Suitable strong bases for this reaction include metal alkoxides, such as sodium methoxide, sodium ethoxide, lithium ethoxide, lithium t-butoxide, and potassium t-butoxide; sodium hydride; alkyllithiums, such as n-butyllithium, t-butyllithium, sec-butyllithium, and methyllithium; and metal amides, such as sodium amide, magnesium diisopropylamide, and lithium diisopropylamide. The preferred base for this transformation is n-butyllithium. This deprotonation reaction is carried out in a dry organic solvent, such as tetrahydrofuran or 1,2-dimethoxyethane, at a temperature of about $-25°$ C.

The benzylic anion is condensed, without isolation, with a benzaldehyde compound of the formula p-$R_1$($C_6H_4$)CHO, wherein $R_1$ is as defined above. Preferably, about one equivalent of the benzaldehyde is added to the cold solution prepared as described in the preceding paragraph. The resulting diastereomeric mixture of condensation products may be isolated, or preferably used in the next step without isolation.

The condensation product is reacted with an acid chloride to produce an intermediate compound. The condensation product is optionally treated with a base, such as n-butyllithium, and reacted with an acid chloride. Representative acid chlorides include acyl chlorides, such as acetyl chloride and benzoyl chloride; sulfonyl chlorides, such as methanesulfonyl chloride, benzenesulfonyl chloride, 1-butanesulfonyl chloride, ethanesulfonyl chloride, isopropylsulfonyl chloride, and p-toluenesulfonyl chloride; alkoxycarbonyl chlorides, such as methoxycarbonyl chloride and benzyloxycarbonyl chloride; and dialkylaminocarbonyl chlorides, such as N,N-dimethylaminocarbonyl chloride; preferably a sulfonyl chloride. The acid chloride is added to the cold reaction mixture, then the resulting mixture is allowed to warm to room temperature. Preferably, methanesulfonyl chloride is added to the reaction mixture shortly after formation of the condensation product, which eliminates the need to add additional base.

The resulting intermediate compound is reacted with a second strong base to produce the E and Z styryl sulfoxides, formula II compounds where $R_1$, $R_2$, and $R_3$ are as defined above. Representative second strong bases for this elimination reaction include metal alkoxides, such as sodium methoxide, sodium ethoxide, lithium ethoxide, lithium t-butoxide, and potassium t-butoxide; sodium hydride; alkyllithiums, such as n-butyllithium, t-butyllithium, sec-butyllithium, and methyllithium; and metal amides, such as sodium amide, magnesium diisopropylamide, and lithium diisopropylamide. The preferred base for this transformation is potassium t-butoxide. Preferably, a 20% excess, such as 1.2 equivalents, of the second base are added. Generally, this reaction is carried out at a temperature of about $15°$ C. to about room temperature, preferably at room temperature.

The compounds of the present invention can be prepared from the formula II compounds. The novel sulfenate silyl esters are prepared from the styryl sulfoxides as shown in Scheme 4.

Scheme 4

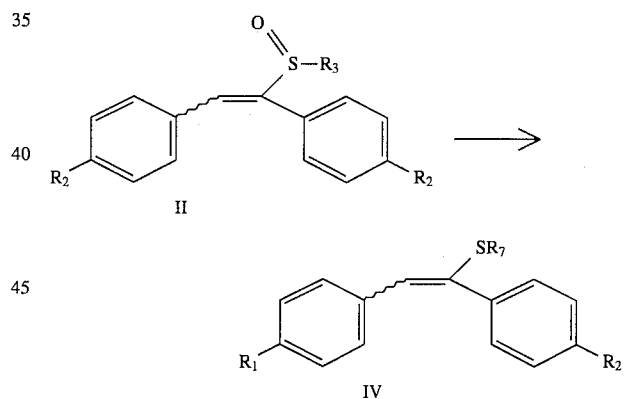

Generally, the sulfenate silyl esters, where $R_1$, $R_2$, and $R_7$ are as defined above and $R_3$ is a thermally-labile or acid-labile $C_1$–$C_{10}$ alkyl, $C_4$–$C_{10}$ alkenyl, or aryl($C_1$–$C_{10}$ alkyl) group, are prepared by reacting a formula II compound with a silylating reagent. Suitable solvents for this reaction include benzene, toluene, xylene, and high-boiling, halogenated hydrocarbon solvents, having a boiling point greater than or equal to $80°$ C., such as 1,1,2-trichloroethane. Suitable silylating reagents include bis(trialkylsilyl)ureas, such as 1,3-bis(trimethylsilyl)urea, 1,3-bis(triethylsilyl)-urea, 1,3-bis(dimethylisopropylsilyl)-urea, 1,3-bis(t-butyldimethylsilyl)urea; bis(triarylsilyl)-ureas, such as 1,3-bis-(triphenylsilyl)urea; bis(dialkylaryl-silyl)ureas, such 1,3-bis(diphenylmethylsilyl)urea; and hexaalkyldisilylzanes, such as hexamethyldisilylzane; or combination of a hexaalkyldisilylzane and a catalytic amount of a chlorotrialkylsilane, such as chlorotrimethylsilane. For best results, the final concentration, after complete addition, of the formula II compound is about 0.001M to about 0.5M. Preferably, a slight excess, such as ten percent, of the silylating reagent is used. This reaction can be carried out at about 80° C. to about 140° C. for about ten minutes to about two hours. Because the Z isomer reacts much faster than the corresponding E isomer, the use of only the Z isomer as the starting compound requires less time for complete transformation.

The novel sulfenamides are prepared from the sulfenate silyl esters as shown in Scheme 5.

Scheme 5

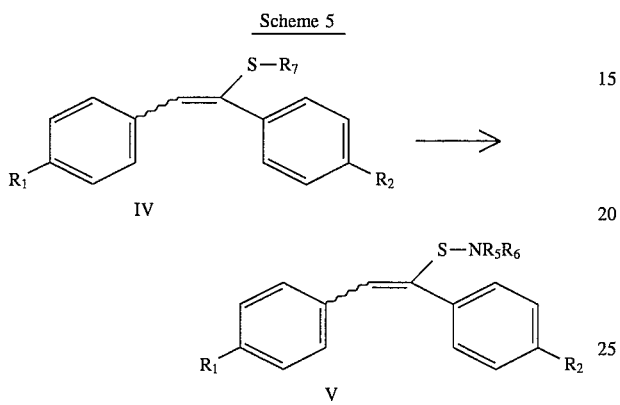

Generally, the sulfenate silyl ester, where $R_1$, $R_2$, and $R_7$ are as defined above, is prepared from the styryl sulfoxide and, preferably without isolation or purification, reacted with an amine of the formula $HNR_5R_6$, wherein $R_5$ and $R_6$ as defined above. Typically, the sulfenate silyl ester is prepared, the reaction solution cooled to about 0° C. to about 50° C., and treated with the amine. Preferably, one to two equivalents of the amine are used. The conversion from the silyl ester to the sulfenamide is typically complete after about two hours to about eight hours. The resulting sulfenamides can be purified using standard organic techniques, such as silica-gel chromatography.

The novel disulfides are prepared from the sulfenate silyl esters as shown in Scheme 6.

Scheme 6

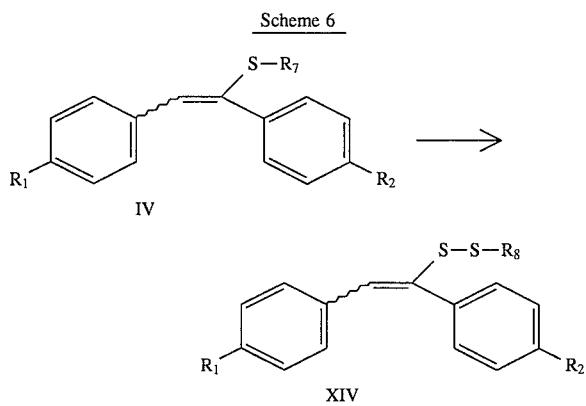

Generally, the sulfenate silyl ester, where $R_1$, $R_2$, and $R_7$ are as defined above, is prepared from the styryl sulfoxide and, preferably without isolation or purification, reacted with a mercaptan of the formula $HSR_8$, where $R_8$ is as defined above, in the presence of an amine base. Preferably, the sulfenate silyl ester is prepared, the reaction solution allowed to cool to room temperature, and the reaction mixture treated with a solution containing the mercaptan and amine base. The solvent for this mercaptan/amine solution is the same as the solvent for the sulfenate silyl ester-containing mixture. Representative amine bases include triethylamine, diisopropylethylamine, pyridine, morpholine, N-methylmorpholine, and collidine. The conversion of the sulfenate silyl ester is typically complete after about one to about eight hours. The resulting disulfides can be purified using standard organic techniques, such as silica-gel chromatography.

The intermediate sulfenate silyl esters, sulfenamides, and disulfides are useful for the synthesis of 2-arylbenzo[b]thiophenses as shown in Scheme 7.

Scheme 7

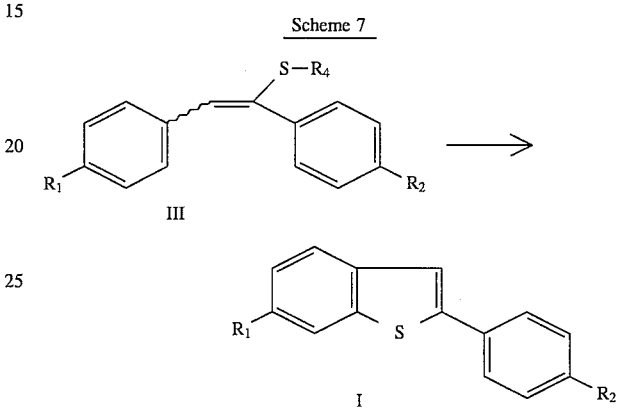

Generally, the sulfenate silyl esters, sulfenamides, or disulfides are treated with acid catalysts to produce the formula I compounds. Suitable acid catalysts for this reaction include Lewis acids or Brønsted acids. Representative Lewis acids include zinc chloride, zinc iodide, aluminum chloride, and aluminum bromide. Representative Brønsted acids include inorganic acids, such as sulfuric and phosphoric acids; carboxylic acids, such as acetic and trifluoroacetic acids; sulfonic acids, such as methanesulfonic, benzenesulfonic, 1-naphthalenesulfonic, 1-butanesulfonic, ethanesulfonic, 4-ethylbenzenesulfonic, 1-hexanesulfonic, 1,5-naphthalenedisulfonic, 1-octanesulfonic, camphorsulfonic, trifluoromethanesulfonic, and p-toluenesulfonic acids; and polymeric arylsulfonic acids, such as Nafion®, Amberlyst®, or Amberlite®. The more preferred acid catalysts are sulfonic acids, such as methanesulfonic acid, benezene-sulfonic acid, camphorsulfonic, and p-toluenesulfonic acid. The most preferred acid catalyst is p-toluenesulfonic acid. Typically, a solution of the acid catalyst in an organic solvent, such as toluene, benzene, xylene, or a high-boiling halogenated hydrocarbon solvent, such as 1,1,2-trichloroethane, is heated to about 80° C. to about 140° C., and treated with a solution of the sulfenate silyl ester, sulfenamide, or disulfide in the same solvent. An excess amount of the acid catalyst is used, preferably three equivalents of the acid. For best results, the final concentration of the starting compound is about 0.01M to about 0.2M, preferably 0.05M. Furthermore, best yields are obtained when the sulfenate silyl ester is slowly added to the heated acid solution over a period of about 15 minutes to about three hours. For best results, residual water is removed from the reaction solution by the use of a Dean-Stark trap or Soxhlet extractor.

The styryl sulfoxides are also useful for the preparation of a benzothiophene styryl sulfide as shown in Scheme 8.

Scheme 8

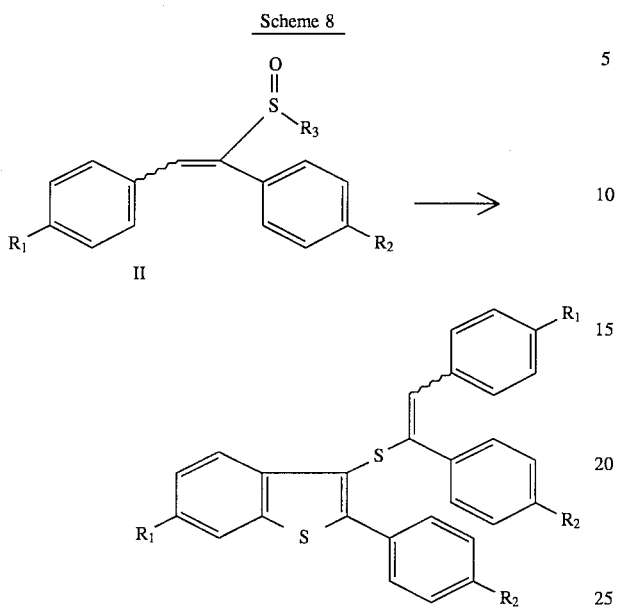

Scheme 9

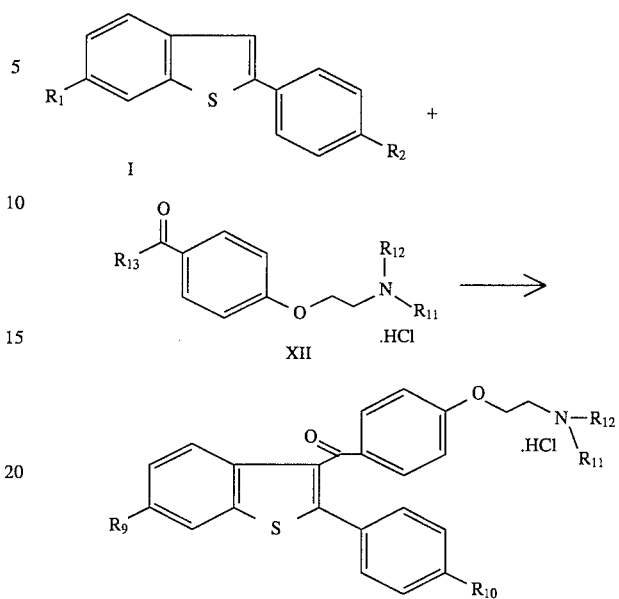

These benzothiophene styryl sulfides, where $R_1$ and $R_2$ are as defined above, are prepared from the styryl sulfoxides. Generally, a solution of the styryl sulfoxide, where $R_1$ and $R_2$ are as defined above and $R_3$ is a thermally-labile or acid-labile $C_1-C_{10}$ alkyl, $C_4-C_{10}$ alkenyl, or aryl($C_1-C_{10}$ alkyl) group, is added to a solution of an acid catalyst at a temperature of about 100° C. to about 140° C., where the acid catalyst is defined above. The concentration of acid catalyst is dependent on the final concentration of the formula II compound and the rate of addition of the formula II compound. When the styryl sulfoxide is at a final concentration of about 0.2M and is added over six hours, the acid concentration is about 0.002M. When the styryl sulfoxide is at a final concentration of about 0.05M and is added over 30 minutes, the acid concentration is about 0.025M. Significant quantities of the formula VI compounds are present in the reaction after about one to two hours. Longer reaction times lead to the production of the formula I compounds.

These formula VI compounds may be subsequently converted to the formula I compounds by treatment with additional acid, such as about 0.5 to about three equivalents, and heating to about 100° C. to about 140° C. The concentration of the formula VI compound is in the range of about 0.01M to about 0.5M. Suitable solvents for both the formation of the formula VI compounds and their conversion to formula I compounds include toluene, xylene, and 1,2-dichloroethane.

The formula I compounds are useful as intermediates in the synthesis of a series of 3-aroyl-2-arylbenzo[b]thiophenes. U.S. Pat. Nos. 4,133,814 and 4,418,068, which are incorporated herein by reference, described these 3-aroyl-2-arylbenzo[b]thiophenes, as well as methods for their preparation from the formula I compounds. An improved synthesis of a group of these 3-aroyl-2-arylbenzo[b]-thiophenes from the formula I compounds, wherein $R_1$ and $R_2$ are hydrogen, $C_1-C_4$ alkoxy, or arylalkoxy, is outlined in Scheme 9.

The Formula I compound, wherein $R_1$ and $R_2$ are hydrogen, $C_1-C_4$ alkoxy, or arylalkoxy, is acylated with the formula XII compound, wherein $R_{13}$ is chloro or hydroxy, in the presence of boron trichloride or boron tribromide; boron trichloride is preferred. The reaction can be carried out in a variety of organic solvents, such as chloroform, methylene chloride, 1,2-dichloroethane, 1,2,3-dichloropropane, 1,1,2, 2-tetrachloroethane, 1,2-dichlorobenzene, chlorobenzene, and fluorobenzene. The preferred solvent for this synthesis is 1,2-dichloroethane. The reaction is carried out at a temperature of about −10° C. to about 25° C., preferably at 0° C. The reaction is best carried out at a concentration of the benzothiophene formula I compound of about 0.2M to about 1.0M. The acylation reaction is generally complete after about two hours to about eight hours.

When $R_1$ and/or $R_2$ is a $C_1-C_4$ alkoxy or arylalkoxy group, the acylated benzothiophene preferably is converted to a formula XIII compound, wherein $R_5$ and/or $R_6$ are hydroxy, without isolation of the product from the acylation reaction. This conversion is performed by adding additional boron trichloride or boron tribromide and heating the reaction mixture. Preferably, two to five molar equivalents of boron trichloride are added to the reaction mixture, most preferably three molar equivalents. This reaction is carried out at a temperature of about 25° C. to about 40° C., preferably at 35° C. The reaction is generally complete after about 4 hours to about 48 hours.

The acylation reaction or acylation/dealkylation reaction is quenched with an alcohol or a mixture of alcohols. Suitable alcohols for use in quenching the reaction include methanol, ethanol, and isopropanol. Preferably, the acylation/dealkylation reaction mixture is added to a 95:5 mixture of ethanol and methanol (3A ethanol). The 3A ethanol can be at room temperature or heated to reflux, preferably at reflux. When the quench is performed in this manner, the Formula XIII compound conveniently crystallizes from the resulting alcoholic mixture. Generally, 1.25 mL to 3.75 mL of alcohol per millimole of the benzothiophene starting material are used.

The following examples further illustrate the present invention. The examples are not intended to be limiting to the scope of the invention in any respect, and should not be so construed. All experiments were run under positive pressure of dry nitrogen. All solvents and reagents were used as obtained. The percentages are generally calculated on a weight (w/w) basis; except for high performance liquid chromatography (HPLC) solvents which are calculated on a volume (v/v) basis. Proton nuclear magnetic resonance ($^1$H NMR) spectra and $^{13}$C nuclear magnetic resonance ($^{13}$C NMR) spectra were obtained on a Bruker AC-300 FTNMR spectrometer at 300.135 MHz or at 75.469 MHz for proton and carbon, respectively, or a GE QE-300 spectrometer at 300.15 MHz. Silica-gel flash chromatography was performed as described by Still et al. using Silica Gel 60 (230–400 mesh, E. Merck). Still et al., *J. Org. Chem.*, 43, 2923 (1978). Elemental analyses for carbon, hydrogen, and nitrogen were determined on a Control Equipment Corporation 440 Elemental Analyzer. Elemental analyses for sulfur were determined on a Brinkman Colorimetric Elemental Analyzer. Melting points were determined in open glass capillaries on a Mel-Temp II melting point apparatus or a Mettler FP62 Automatic instrument, and are uncorrected. Field desorption mass spectra (FDMS) were obtained using a Varian Instruments VG 70-SE or VG ZAB-3F mass spectrometer. High resolution free atom bombardment mass spectra (FABMS) were obtained using a Varian Instruments VG ZAB-2SE mass spectrometer.

The in situ yields of 6-methoxy-2-(4-methoxyphenyl-)benzo[b]thiophene were determined by high performance liquid chromatography (HPLC) in comparison to an authentic sample of this compound prepared by published synthetic routes. See U.S. Pat. No. 4,133,814. Generally, samples of the reaction mixture was diluted with acetonitrile and the diluted sample assayed by HPLC using a Zorbax® RX-C8 column (4.6 mm×25 cm) with UV detection (280 nm). The following linear-gradient solvent system was used for this analysis:

| Gradient Solvent System | | |
|---|---|---|
| Time (min) | A (%) | B (%) |
| 0 | 50 | 50 |
| 2 | 50 | 50 |
| 20 | 20 | 80 |
| 35 | 20 | 80 |
| 37 | 50 | 50 |
| 45 | 50 | 50 |

A: 0.01M aqueous sodium phosphate (pH 2.0)
B. acetonitrile

The amount (percentages) of 6-hydroxy-2-(4-hydroxyphenyl)-3 -[4-(2-piperidinoethoxy)benzoyl]-benzo[b]thiophene hydrochloride in the crystalline material (potency) was determined by the following method. A sample of the crystalline solid (5 mg) was weighed into a 100-mL volumetric flask, and dissolved in a 70/30 (v/v) mixture of 75 mM potassium phosphate buffer (pH 2.0) and acetonitrile. An aliquot of this solution (10 μL) was assayed by high performance liquid chromatography, using a Zorbax® Rx-C8 column (25 cm×4.6 mm ID, 5 μparticle) and UV detection (280 nm). The following gradient solvent system was used:

| Gradient Solvent System (Potency) | | |
|---|---|---|
| Time (min) | A (%) | B (%) |
| 0 | 70 | 30 |
| 12 | 70 | 30 |
| 14 | 25 | 75 |
| 16 | 70 | 30 |
| 25 | 70 | 30 |

A: 75 mM KH$_2$PO$_4$ buffer (pH 2.0)
B: acetonitrile

The percentage of 6-hydroxy-2-(4-hydroxyphenyl)-3-[4-(2-piperidinoethoxy)benzoyl]benzo[b]thiophene hydrochloride in the sample was calculated using the peak area, slope (m), and intercept (b) of the calibration curve with the following equation:

$$\% \text{ potency} = \frac{\text{peak area} - b}{m} \times \frac{\text{sample volume (mL)}}{\text{sample weight (mg)}}$$

The amount (percentage) of solvent, such as 1,2-dichloroethane, present in the crystalline material was determined by gas chromatography. A sample of the crystalline solid (50 mg) was weighed into a 10-mL volumetric flask, and dissolved in a solution of 2-butanol (0.025 mg/mL) in dimethylsulfoxide. A sample of this solution was analyzed on a gas chromatograph using a DB Wax column (30 m×0.53 mm ID, 1 μparticle), with a column flow of 10 mL/min and flame ionization detection. The column temperature was heated from 35° C. to 230° C. over a 12 minute period. The amount of solvent was determined by comparison to the internal standard (2-butanol).

EXAMPLE 1

E-t-Butyl 4,4'-Dimethoxystilbenyl Sulfoxide

A. Preparation of E-t-Butyl 4,4'-Dimethoxystilbenyl Sulfide

A solution of desoxyanisoin (12.82 g) in tetrahydrofuran (100 mL) was treated with titanium (IV) chloride (10.43 g). During the dropwise addition of titanium (IV) chloride, the reaction mixture was cooled to maintain the temperature below 35° C. Upon complete addition, the resulting mixture was stirred at 30° C. After an additional 30 minutes, this mixture was treated with a solution of 2-methyl-2-propanethiol (6.76 mL) and triethylamine (16.70 mL) in tetrahydrofuran (15 mL). The resulting mixture was stirred at 50° C. After two hours, the mixture was added to ten percent sodium carbonate (500 mL). The resulting mixture was extracted with methylene chloride. The combined methylene chloride extracts were dried over magnesium sulfate, filtered, and concentrated in vacuo to give 17.2 g of an oil, which crystallized upon cooling to room temperature. This crystalline material was recrystallized from hot ethanol to give 12.3 g of the title compound. Melting point 71°–73° C.

Analysis calculated for C$_{20}$H$_{24}$O$_2$S: C, 73.13; H, 7.36; S, 9.76. Found: C, 73.37; H, 7.51; S, 9.87.

B. Preparation of E-t-Butyl 4,4'-Dimethoxystilbenyl Sulfoxide

The crystalline compound prepared as described in Example 1A was dissolved in toluene (150 mL), and the resulting solution cooled to about −20° C. The cold solution was treated with peracetic acid (32% w/w in dilute acetic acid, 1.24 g) over ten minutes. The resulting mixture was extracted with saturated sodium sulfite and brine. The organic phase was concentrated in vacuo. The residue was recrystallized from ethyl acetate/heptane to give 14.11 g of the title compound. Melting point 104° C. (dec).

Analysis calculated for $C_{20}H_{24}O_3S$: C, 69.74; H, 7.02; S, 9.31. Found: C, 69.47; H, 7.04; S, 9.54.

EXAMPLE 2

Z-t-Butyl 4,4'-Dimethoxystilbenyl Sulfoxide

A. Preparation of t-Butyl 4-Methoxybenzyl Sulfide

A mixture of 4-methoxybenzyl alcohol (10.13 g) and zinc iodide (11.7 g) in 1,2-dichloroethane (120 mL) was treated with 2-methyl-2-propanethiol (9.92 mL) in one portion. The resulting mixture was stirred at room temperature. After about 18 hours, the reaction was diluted with water (100 mL) and methylene chloride 100 mL). The organic phase was removed, dried over magnesium sulfate, filtered, and concentrated in vacuo to give 14.4 g of an oil.

$^1$H NMR (CDCl$_3$): δ7.28 (d, 2H), 6.85 (d, 2H), 3.77 (s, 3H), 3.73 (s, 2H), 1.36 (s, 9H). $^{13}$C NMR (CDCl$_3$): δ130, 114, 56, 35, 32.

Analysis calculated for $C_{12}H_{18}OS$: C, 68.52; H, 8.63. Found: C, 68.80; H, 8.67.

B. Preparation of Z-t-Butyl 4,4'Dimethoxystilbenyl Sulfide

A solution of the compound prepared as described in Example 2A (2.51 g) in tetrahydrofuran (50 mL) was cooled to about −20° C. This cold solution was treated with a solution of n-butyllithium in hexane (1.6M, 7.47 mL) over ten minutes. The resulting solution was allowed to warm to about 0° C. over 35 minutes. This cold solution was treated with p-anisaldehyde (1.46 mL). After an additional 15 minutes, the reaction solution was treated with methanesulfonyl chloride (0.95 mL). The resulting reaction was allowed to warm to room temperature. After an additional 45 minutes, the reaction mixture was treated with a solution of potassium t-butoxide in tetrahydrofuran (1.0M, 12.0 mL). After an additional 45 minutes, the reaction was quenched by the addition of 1N hydrochloric acid (12.0 mL). The organic phase was separated, dried over magnesium sulfate, filtered, and concentrated to an oil (4.4 g). $^1$H NMR (CDCl$_3$): δ7.95 (d, H), 7.05 (s, H), 6.9 (d, H), 6.8 (dd, 2H), 3.75 (s, 3H), 0.95 (s, 9H). $^{13}$C NMR (CDCl$_3$): δ8153, 139, 137, 114, 56, 32.

C. Preparation of Z-t-Butyl 4,4'-Dimethoxystilbenyl Sulfoxide

The compound from Example 2B was converted to the title compound using the procedure substantially as described in Example 1B. $^1$H NMR (CDCl$_3$): δ7.61 (d, H), 7.56 (d, X), 7.1 s, H 6.9 (dd, 2H), 3.83 (s, 3H), 1.05 (s, 9H) . $^{13}$C NMR (CDCl$_3$): δ142, 132.5, 131, 118, 117, 56, 24.

Analysis calculated for $C_{20}H_{24}O_3S$: C, 69.74; H, 7.02. Found: C, 69.98; H, 6.94.

EXAMPLE 3

E and Z-t-Butyl 4,4'-Dimethoxystilbenyl Sulfoxide

A. Preparation of t-Butyl 4-Methoxybenzyl Sulfide

A mixture of 4-methoxybenzyl alcohol (10.13 g) and zinc iodide (11.7 g) in 1,2-dichloroethane (120 mL) was treated with 2-methyl-2-propanethiol (9.92 mL) in one portion. The resulting mixture was stirred at room temperature. After about 18 hours, the reaction was diluted with water (100 mL) and methylene chloride (100 mL). The organic phase was removed, dried over magnesium sulfate, filtered, and concentrated in vacuo to give 14.4 g of an oil. $^1$H NMR (CDCl$_3$): δ7.28 (d, 2H), 6.85 (d, 2H) , 3.77 (s, 3H), 3.73 (s, 2H), 1.36 (s, 9H). $^{13}$C NMR (CDCl$_3$): δ130, 114, 56, 35, 32.

Analysis calculated for $C_{12}H_{18}OS$: C, 68.52; H, 8.63. Found: C, 68.80; H, 8.67.

B. Preparation of t-Butyl 4-Methoxybenzyl Sulfoxide

A solution of the compound prepared as described in Example 3A (14.4 g) in 1,2-dichloroethane (50 mL) was cooled to about 5° C. and the cold solution treated with peracetic acid (32% w/w in dilute acetic acid, 14.2 mL) over 30 minutes. Upon complete addition of the peracetic acid, the reaction was treated with brine and sodium bicarbonate. The organic phase was removed, dried over magnesium sulfate, filtered, and concentrated to a yellow precipitate. This residue was treated with hexane (100 mL) and the resulting mixture stirred at room temperature. After about 18 hours, the mixture was filtered and the solids washed with hexane (100 mL). The solid material was dried in vacuo to give 14.07 g of the title compound. Melting point 124°–126° C. $^1$H NMR (CDCl$_3$): δ7.26 (d, 2H), 6.89 (d, 2H), 3.79 (d, H), 3.78 (s, 3H), 3.58 (d, H), 1.3 (s, 9H). $^{13}$C NMR (CDCl$_3$): δ132, 114, 56, 53, 23.

Analysis calculated for $C_{12}H_{18}O_2S$: C, 63.68; H, 8.02. Found: C, 63.72; H, 7.93.

C. Preparation of E and Z-t-Butyl 4,4'-Dimethoxystilbenyl Sulfoxide

A solution of the compound prepared as described in Example 3B (10.0 g) in tetrahydrofuran (140 mL) was cooled to about −30° to −25° C. (dry ice/acetone bath). This cold solution was treated with n-butyllithium in cyclohexane (1.6M, 27.65 mL) over 25 minutes. After stirring for 35 minutes, the reaction mixture was treated with p-anisaldehyde (5.4 mL). The dry ice/acetone bath was removed and the reaction allowed to warm to about 20° C. This mixture was treated with methanesulfonyl chloride (3.5 mL). The temperature of the reaction rose from about 20° to about 35° C. upon addition of the methanesulfonyl chloride. The mixture was cooled to about 25° C., then treated with potassium t-butoxide in tetrahydrofuran (1M, 50.9 mL). After stirring for an additional 35 minutes, the reaction was treated with 1N hydrochloric acid (51.0 mL). The phases were separated, and the organic layer dried over magnesium sulfate, filtered, and concentrated to an oil (16.67 g). This material was used in the next step without further purification. The carbon and proton NMR spectra were similar to that obtained for the compound prepared as described in Examples 1 and 2.

EXAMPLE 4

E and Z-Trimethylsilyl 4,4'-Dimethoxystilbenyl Sulfenate

A mixture of the compound prepared as described in Example 1 (350 mg) and 1,3-bis(trimethylsilyl)urea (116 mg) in toluene (11 mL) was heated to reflux. After 1.5 hours, the reaction mixture was allowed to cool to room temperature, filtered, and the filtrate concentrated in vacuo to give a 7:1 mixture of E/Z regioisomers of the title compounds.

FDMS: m/z=361 (M+1).

E Isomer:
$^1$H NMR (d$_6$-benzene): δ7.39 (d, 2H), 7.10 d, 3H), 6.68 (d, 2H), 6.68 (s, 1H), 6.57 (d, 2H), 3.18 (s, 3H), 3.17 (s, 3H), 0.23 (s, 9H).

Z Isomer:
$^1$H NMR (d$_6$-benzene): δ7.71 (d, 2H), 7.31 d, 2H), 6.85 (d, 2H), 6.79 (d, 2H), 6.60 (s, 1H), 3.28 (s, 3H), 3.26 (s, 3H), −0.05 (s, 9H).

EXAMPLE 5

E and Z-Trimethylsilyl 4,4'-Dimethoxystilbenyl Sulfenate

A mixture of the compound prepared as described in Example 2 and 1,3-bis(trimethylsilyl)urea in toluene was heated to reflux. After ten minutes, the mixture was allowed to cool, filtered, and concentrated in vacuo to give a 7:1 mixture of E/Z regioisomers of the title compounds.

E Isomer:
$^{13}$C NMR (d$_6$-benzene, 8° C.): δ160.49, 158.53, 141.54, 131.97, 129.91, 129.65, 125.59, 116.41, 114.68, 113.98, 54.56, −0.09.

EXAMPLE 6

E and Z-N,N-Dimethyl-4,4'-Dimethoxystilbenyl Sulfenamide

A mixture of the compound prepared as described in Example 1 (1.74 g) and 1,3-bis(trimethylsilyl)urea (578 mg) in toluene (54 mL) was heated to reflux. After 1.5 hours, the reaction was allowed to cool to room temperature, and treated with dimethylamine (2.80 mL, 2.0M in tetrahydrofuran). After an additional two hours, the reaction solution was evaporated to dryness to give a 7:1 mixture of E/Z regioisomers of the title compounds. This residual mixture was purified using silica-gel flash chromatography, eluting with a mixture of ethyl acetate/hexane (9:1), to give 1.06 g of the title compounds as an 8:1 mixture of E/Z regioisomers.

FDMS: m/z=315 ( M$^+$).

Analysis calculated for C$_{18}$H$_{21}$NO$_2$S: C, 68.54; H, 6.71; N, 4.44. Found: C, 68.40; H, 6.69; N, 4.22.

E Isomer:
$^1$H NMR (d$_6$-benzene ): δ7.44 (d, 2H), 7.11 (d, 2H), 6.99 (s, 1H), 6.71 (d, 2H), 6.56 (d, 2H), 3.22 (s, 3H), 3.18 (s, 3H), 2.66 (s, 6H).

$^{13}$C NMR (d$_6$-benzene): δ160.00, 158.83, 139,70, 131.48, 130.78, 130.51, 129.94, 123.77, 114.55, 113.97, 54.63, 54.61, 48.17.

Z Isomer:
$^1$H NMR (d$_6$-benzene): δ7.61 (d, 4H), 6.82 (d, 2H), 6.80 (d, 2H), 6.80 (s, 1H), 3.32 (s, 3H), 3.27 ( s, 3H), 2.41 (s, 6H).

$^{13}$C NMR (d$_6$-benzene): δ159.89, 159.30, 139.76, 136.46, 131.94, 131.82, 130.22, 130.20, 113.83, 113.76, 54.81, 54.73, 48.61.

EXAMPLE 7

E and Z-N-Benzyl-4,4'-Dimethoxystilbenyl Sulfenamide

A mixture of the compound prepared as described in Example 1 (1.74 g) and 1,3-bis(trimethylsilyl)urea (578 mg) in toluene (54 mL) was heated to reflux. After 1.5 hours, the reaction was allowed to cool to room temperature, and treated with benzylamine 0.575 mL). After an additional two hours, the reaction solution was evaporated to dryness to give a 7:1 mixture E/Z of regioisomers of the title compounds. This residual mixture was purified using silica-gel flash chromatography, eluting with a mixture of ethyl acetate/hexane (7:1), to give 1.06 g of the title compounds as a 6:1 mixture of E/Z regioisomers.

Analysis calculated for C$_{23}$H$_{23}$NO$_2$S: C, 73.18; H, 6.14; N, 3.71. Found: C, 73.16; H, 6.18; N, 3.50

E Isomer:
$^1$H NMR (d$_6$-benzene ): δ7.41 ( d, 2H), 7.13 (d, 2H), 7.12–7.03 (m, 5H), 6.87 (s, 1H), 6.71 (d, 2H),6.59 (d, 2H),3.89 (d, 2H), 3.23 (s, 3H), 3.20 (s, 3H),2.71 ( t, 1H) .

$^{13}$C NMR (d$_6$-benzene): δ159.98, 158.91, 140.53, 139.77, 131.45, 130.50, 129.87, 128.77, 128.66, 128.59, 127.53, 123.10, 114.74, 114.02, 56.14, 54.69, 54.64.

Z Isomer:
$^1$H NMR (d$_6$-benzene): δ7.59 (d, 2H), 7.53 (d, 2H), 7.01–6.91 (m, 5H), 6.83 (s, 1H), 6.79 (d, 2H), 6.77 (d, 2H),3.62 (d, 2H), 3.31 (s, 3H), 3.27 (s, 3H), 2.82 (t, 1H).

$^{13}$C NMR (d$_6$-benzene): δ160.05, 159.14, 140.48, 139.27, 132.50, 131.32, 130.04, 129.86, 128.87, 128.58, 128.46, 127.49, 114.48, 114.00, 56.23, 54.90, 54.78.

EXAMPLE 8

6-Methoxy-2-(4-methoxyphenyl)benzo[b]thiophene

A solution of p-toluenesulfonic acid monohydrate (552 mg) was added to toluene (15 mL) and heated to reflux, and water was removed by allowing it to collect in a Dean-Stark trap. This refluxing solution was treated with a solution of the regioisomeric compounds prepared as described in Example 4 (523 mg) in toluene (15 mL) over 15 minutes. Upon complete addition, an aliquot was removed for HPLC analysis. This analysis showed a 46.6% in situ yield of the title compound.

EXAMPLE 9

6 -Methoxy-2-(4-methoxyphenyl)benzo[b]thiophene

A solution of p-toluenesulfonic acid monohydrate (1.26 g) in toluene (20 mL) was heated to reflux, and water was removed by allowing it to collect in a Dean-Stark trap. A solution of the regioisomeric compounds prepared as described in Example 6 (650 mg) in toluene (9 mL) was added to the refluxing acid solution over 1.8 hours. The reaction solution was treated with ethanol (10 mL), and the resulting mixture allowed to cool to room temperature. The resulting slurry was stirred at room temperature. After about 18 hours, the mixture was cooled to about 5° C., and filtered to give 290 mg of the title compound. Melting point 199°–200° C.

$^1$H NMR (d$_6$-DMSO): δ67.7 (d, 1H), 7.64 (d, 2H), 7.61 (s, 1H), 7.52 (d, 1H), 7.01 (d, 2H), 6.98 dd, 1H), 3.81 (s, 3H), 3.79 (s, 3H).

Analysis calculated for C$_{16}$H$_{14}$O$_2$S: C, 71.09; H, 5.22. Found: C, 71.09; H, 5.27.

EXAMPLE 10

E and Z-3-(4,4'-Dimethoxystilbenyl sulfide)-6-methoxy-2-(4 -methoxyphenyl)benzo[b]thiophene A solution of p-toluenesulfonic acid monohydrate (552 mg) in toluene (111 mL) was heated to reflux, and water was removed by allowing it to collect in a Dean-Stark trap. A solution of the compound prepared as described in Example 1 (10 g) in toluene (34 mL) was added to the refluxing acid solution over six hours. After an additional two hours, the mixture was cooled to 0° C. After an additional 18 hours, the cold mixture was filtered to remove the precipitated 6-methoxy-2 -(4-methoxyphenyl)benzo[b]thiophene. The filtrate was extracted with an equal volume of saturated sodium bicarbonate solution. The organic phase was separated, dried over sodium sulfate, filtered, and concentrated in vacuo to give 4.8 g of an orange oil. This oil was divided into two parts and each purified using silica-gel flash chromatography, eluting with hexane/ethyl acetate (3.5:1). The fractions contained in the desired regioisomers were concentrated to an oil. This oil was treated with diethyl ether to selectively crystallize the early-eluting regioisomer (155 mg). The mother liquor from these crystallizations were enriched in the late-eluting regioisomer.

Early-eluting Isomer $^1$H NMR (CDCl$_3$): δ7.71 (d, 2H), 7.64 (d, 1H), 7.46 (d, 2H), 7.06 (d, 1H), 6.94 (d, 2H), 6.92 (d, 2H), 6.90 (m, 1H), 6.85 (d, 2H), 6.59 (s, 1H), 6.45 (d, 2H), 3.86 (s, 3H), 3.85 (s, 3H), 3.80 (s, 3H), 3.66 (s, 3H).

High resolution FABMS calculated for C$_{32}$H$_{29}$O$_4$S$_2$ (MH$^+$) 541.1507. Found: 541.1491.

Late-eluting Isomer $^1$H NMR (CDCl$_3$): δ7.90 (d, 1H), 7.62 (d, 2H), 7.24 (1H), 7.08 (d, 2H), 7.02 (dd, 1H), 6.96 (d, 2H), 6.74–6.71 (d, 2H), 6.70 (d, 2H), 6.55 (d, 2H), 6.21 s, 1H), 3.86 (s, 3H), 3.85 (s, 3H), 3.76 (s, 3H), 3.67 s, 3H).

FDMS: m/z=540 (m$^+$)

EXAMPLE 11

6-Methoxy-2-(4-methoxyphenyl)benzo[b]thiophene

The compound (early-eluting isomer) prepared as described in Example 10 (125 mg) was added to a refluxing solution of p-toluenesulfonic acid monohydrate (4.2 mg) in toluene (1.5 mL). After six hours, methanesulfonic acid (7.5 μL) was added to the reaction mixture. After an additional hour, the reaction mixture was allowed to cool to room temperature. The resulting mixture was diluted with acetonitrile and assayed by HPLC, showing a 71.1% in situ yield of the title compound.

EXAMPLE 12

6-Hydroxy-2-(4-hydroxyphenyl)-3-[4-(2-piperidino-ethoxy)benzoyl] benzo[b]thiophene Hydrochloride 1,2-Dichloroethane Solvate A. Preparation of Ethyl 4-(2-Piperidinoethoxy)benzoate A mixture of ethyl 4-hydroxybenzoate (8.31 g), 1-(2-chloroethyl)piperidine monohydrochloride (10.13 g), potassium carbonate (16.59 g), and methyl ethyl ketone (60 mL) was heated to 80° C. After one hour, the mixture was cooled to about 55° C. and treated with additional 1-(2-chloroethyl)piperidine monohydrochloride (0.92 g). The resulting mixture was heated to 80° C. The reaction was monitored by thin layer chromatography (TLC), using silica-gel plates and ethyl acetate/acetonitrile/triethylamine (10:6:1, v/v). Additional portions of 1-(2-chloroethyl)piperidine hydrochloride are added until the starting 4-hydroxybenzoate ester is consumed. Upon complete reaction, the reaction mixture was treated with water (60 mL) and allowed to cool to room temperature. The aqueous layer was discarded and the organic layer concentrated in vacuo at 40° C. and 40 mm Hg. The resulting oil was used in the next step without further purification.

B. Preparation of 4-(2-Piperidinoethoxy)benzoic Acid Hydrochloride

A solution of the compound prepared as described in Example 12A (about 13.87 g) in methanol (30 mL) was treated with 5N sodium hydroxide (15 mL), and heated to 40° C. After 4½ hours, water (40 mL) was added. The resulting mixture was cooled to 5°–10° C., and concentrated hydrochloric acid (18 mL) was added slowly. The title compound crystallized during acidification. This crystalline product was collected by filtration, and dried in vacuo at 40°–50° C. to give 83% yield of the title compound. Melting point 270°–271° C.

C. Preparation of 4-(2-Piperidinoethoxy)benzoyl Chloride Hydrochloride

A solution of the compound prepared as described in Example 12B (30.01 g) and dimethylformamide (2 mL) in methylene chloride (500 mL) was treated with oxalyl chloride (10.5 mL) over a 30–35 minute period. After stirring for about 18 hours, the reaction was assayed for completion by HPLC analysis. Additional oxalyl chloride may be added to the reaction if the starting carboxylic acid is present. Upon completion, the reaction solution was evaporated to dryness in vacuo. The residue was dissolved in methylene chloride (200 mL), and the resulting solution evaporated to dryness. This dissolution/evaporation procedure was repeated to give the title compound as a solid.

D. Preparation of 6-Hydroxy-2-(4-hydroxyphenyl)-2-[4-(2-piperidinoethoxy)benzoyl]benzo[b]thiophene Hydrochloride 1,2-Dichloroethane Solvate A mixture of the compound prepared as described in Example 8, 9, or 11 (2.92 g), the compound prepared as described in Example 12C (3.45 g), and 1,2-dichloroethane (52 mL) was cooled to about 0° C. Boron trichloride gas was condensed into a cold graduated cylinder (2.8 mL), and added to the cold mixture described above. After eight hours at 0° C., the reaction mixture was treated with additional boron trichloride (2.8 mL). The resulting solution was heated to 35° C. After 16 hours, the reaction was complete.

Methanol (30 mL) was treated with the reaction mixture from above over a 20-minute period, causing the methanol to reflux. The resulting slurry was stirred at 25° C. After one hour, the crystalline product was filtered, washed with cold methanol (8 mL), and dried at 40° C. in vacuo to give 5.14 g of the title compound. Melting point 225° C.

Potency (HPLC): 86.8%

1,2-Dichloroethane (gas chromatography): 6.5%

EXAMPLE 13

6-Methoxy-2 -(4-methoxyphenyl)benzo[b]thiophene

A solution of p-toluenesulfonic acid monohydrate (1.05 g) in toluene (20 mL) was heated to reflux, and water was removed by allowing it to collect in a Dean-Stark trap. A solution of the regioisomeric compounds prepared as described in Example 7 (780 mg) in toluene (9 mL) was added to the refluxing acid solution over ten minutes. After one hour, the reaction solution was treated with ethanol (10 mL), and the resulting mixture allowed to cool to room temperature. The resulting slurry was stirred at room temperature. After about 18 hours, the mixture was filtered to give 149 mg of the title compound. Melting point 199°–200° C.

Analysis calculated for C$_{16}$H$_{14}$O$_2$S: C, 71.09; H, 5.22. Found: C, 71.05; H, 5.22.

EXAMPLE 4

E and Z-4,4'-Dimethoxystilbenyl Ethyl Disulfide

A solution of the regioisomeric compounds prepared as described in Example 4 (1.83 g) in toluene (54 mL) was treated with ethanethiol (0.433 mL) and triethylamine (0.715 mL). After about 2.5 hours at room temperature, the reaction solution was evaporated to dryness in vacuo to give a mixture of regioisomers. The residue was purified using silica-gel chromatography, eluting with ethyl acetate/hexane (9:1), to give 1.14 g of a 5.7:1 mixture of E/Z regioisomers of the title compounds.

Analysis calculated for $C_{18}H_{20}O_2S_2$: C, 65.03; H, 6.06. Found: C, 65.32; H, 6.28.

E Isomer:
$^1$H NMR ($d_6$-benzene): δ7.35 (d, 2H), 7.19 (s, 1H), 7.05 (d, 2H), 6.72 (d, 2H), 6.54 (d, 2H), 3.21 (s, 3H), 3.14 (s, 3H), 2.39 (q, 2H), 1.09 (t, 3H).
$^{13}$C NMR ($d_6$-benzene): δ160.09, 159.16, 135.95, 131.71, 130.61, 130.16, 129.48, 126.88, 114.54, 113.99, 54.64, 54.61, 32.29, 14.33.

Z Isomer:
$^1$H NMR ($d_6$-benzene): δ7.67 (d, 2H), 7.58 (d, 2H), 6.90 (s, 1H), 6.83 (d, 2H), 6.80 (d, 2H), 3.30 (s, 3H), 3.28 (s, 3H), 2.26 (q, 2H), 0.94 (t, 3H).
$^{13}$C NMR ($d_6$-benzene): δ59.98, 159.53, 137.58, 134.03, 132.79, 131.69, 130.45, 113.91, 113.87, 54.79, 54.73, 32.61, 14.25.

EXAMPLE 15

6-Methoxy-2-(4-methoxyphenyl)benzo[b]thiophene

A solution of p-toluenesulfonic acid monohydrate (1.21 g) in toluene (20 mL) was heated to reflux, and water was removed by allowing it to collect in a Dean-Stark trap. A solution of the regioisomeric compounds prepared as described in Example 14 (685 mg, 5.7:1 regioisomeric mixture) in toluene (9 mL) was added to the refluxing acid solution over 1.8 hours. An aliquot of the mixture was analyzed by HPLC, showing a 23.2% in situ yield of the title compound.

We claim:

1. A compound of the formula

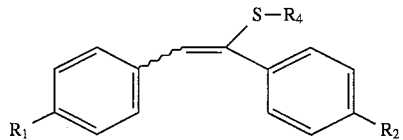

III wherein:
$R_1$ is hydrogen, $C_1-C_4$ alkoxy, arylalkoxy, halo, or amino;
$R_2$ is hydrogen, $C_1-C_4$ alkoxy, arylalkoxy, halo, or amino;
$R_4$ is $OSi(R)_3$, $NR_5R_6$, or $SR_8$;
each R is independently $C_1-C_6$ alkyl, aryl, or arylalkyl;
$R_5$ and $R_6$ are independently hydrogen, $C_1-C_6$ alkyl, arylalkyl, or aryl; or $R_5$ and $R_6$ together with the nitrogen atom form a ring selected from piperidine, pyrrolidine, morpholine, or hexamethylimine; and
$R_8$ is $C_1-C_6$ alkyl, aryl, or arylalkyl.

2. The compound of claim 1 wherein:
$R_1$ is hydrogen, $C_1-C_4$ alkoxy, or arylalkoxy; and
$R_2$ is hydrogen, $C_1-C_4$ alkoxy, or arylalkoxy.

3. The compound of claim 2 wherein:
$R_4$ is $OSi(R)_3$; and
each R is independently $C_1-C_6$ alkyl, aryl, or arylalkyl.

4. The compound of claim 3 wherein $R_4$ is OTMS, OTES, OTIPS, ODMIPS, ODEIPS, OTDS, OTBDMS, OTBDPS, OTBS, OTPS, ODPMS, or OTBMPS.

5. The compound of claim 4 wherein $R_4$ is OTMS, OTES, ODMIPS, ODEIPS, OTBDMS, OTBS, or OTPS.

6. The compound of claim 5 wherein $R_1$ and $R_2$ are $C_1-C_4$ alkoxy.

7. The compound of claim 6 wherein $R_1$ and $R_2$ are methoxy, and $R_4$ is OTMS.

8. The compound of claim 2 wherein:
$R_4$ is $NR_5R_6$; and
$R_5$ and $R_6$ are independently hydrogen, $C_1-C_6$ alkyl, arylalkyl, or aryl; or $R_5$ and $R_6$ together with the nitrogen atom form a ring selected from piperidine, pyrrolidine, morpholine, and hexamethylimine.

9. The compound of claim 8 wherein $R_5$ and $R_6$ are independently hydrogen, $C_1-C_6$ alkyl, or arylalkyl; or $R_5$ and $R_6$ together with the nitrogen atom form a ring selected from piperidine and pyrrolidine.

10. The compound of claim 9 wherein $R_1$ and $R_2$ are $C_1-C_4$ alkoxy.

11. The compound of claim 10 wherein $R_1$ and $R_2$ are methoxy, and $R_5$ and $R_6$ are methyl.

12. The compound of claim 10 wherein $R_1$ and $R_2$ are methoxy, $R_5$ is hydrogen, and $R_6$ is benzyl.

13. The compound of claim 2 wherein:
$R_4$ is $SR_8$; and
$R_8$ is $C_1-C_6$ alkyl, aryl, or arylalkyl.

14. The compound of claim 13 wherein $R_8$ is $C_1-C_6$ alkyl or arylalkyl.

15. The compound of claim 14 wherein $R_8$ is $C_1-C_6$ alkyl.

16. The compound of claim 15 wherein $R_1$ and $R_2$ are $C_1-C_4$ alkoxy.

17. The compound of claim 16 wherein $R_1$ and $R_2$ are methoxy, and $R_8$ is ethyl.

* * * * *

UNITED STATES PATENT AND TRADEMARK OFFICE
CERTIFICATE OF CORRECTION

PATENT NO. : 5,514,826

DATED : May 7, 1996

INVENTOR(S) : David W. Hoard
Wayne D. Luke

It is certified that error appears in the above-indentified patent and that said Letters Patent is hereby corrected as shown below:

Column 10, line 41 in Scheme 4 first $R_2$ reads ... "$R_2$" ... should read -$R_1$-

Column 18, line 61 reads ... "7.10 d, 3H)" ... should read -7.10 d, 2H)-

Column 20, line 45 reads ... "DMSO): δ67.7" ... should read -DMSO): δ7.67

Column 22, line 20 reads ... "(4-hydroxyphenyl)-2-[4" ... should read -(4-hydroxyphenyl)-3-[4-

Column 23, line 18 reads ... "benzene): δ59.98," ... should read -benzene): δ159.98,-

Signed and Sealed this

Twenty-fifth Day of November, 1997

Attest:

BRUCE LEHMAN

Attesting Officer

Commissioner of Patents and Trademarks